United States Patent [19]

Farnham et al.

[11] 4,147,860

[45] Apr. 3, 1979

[54] PROCESS FOR PREPARING NITROAROMATIC GLYCOSIDES

[75] Inventors: William B. Farnham; Alexander L. Johnson, both of Wilmington, Del.

[73] Assignee: E. I. Du Pont de Nemours and Company, Wilmington, Del.

[21] Appl. No.: 898,442

[22] Filed: Apr. 20, 1978

Related U.S. Application Data

[63] Continuation-in-part of Ser. No. 704,974, Jun. 17, 1976, abandoned.

[51] Int. Cl.² .................................................. C07H 15/00
[52] U.S. Cl. ................................ 536/4; 536/115; 536/119; 536/120; 536/122
[58] Field of Search .................... 536/4, 115, 122, 120

[56] References Cited

U.S. PATENT DOCUMENTS

| | | | |
|---|---|---|---|
| 2,094,693 | 10/1937 | Wyler | 536/4 |
| 2,480,785 | 8/1949 | Sowden et al. | 536/4 |
| 2,938,898 | 5/1960 | Werner et al. | 536/115 |

FOREIGN PATENT DOCUMENTS

2602542  7/1976  Fed. Rep. of Germany ............. 536/4

OTHER PUBLICATIONS

Jansen et al., "Nature", vol. 182, No. 4634, Aug. 23, 1958, pp. 525–526.

*Primary Examiner*—Johnnie R. Brown

[57] ABSTRACT

A process for preparing nitroaromatic glycosides is described. The process comprises contacting an acetylated glycoside of maltotetraose, maltopentaose or maltohexaose with a phenol, nitrating the resulting product to place a $NO_2$ group on the aromatic moiety and deacetylating the nitrated product. The nitroaromatic glycosides are useful as standard substrates for the assay of α-amylase.

10 Claims, No Drawings

PROCESS FOR PREPARING NITROAROMATIC GLYCOSIDES

RELATED APPLICATION

This is a continuation-in-part of our copending application Ser. No. 704,974 filed June 17, 1976, now abandoned.

BACKGROUND OF THE INVENTION

1. Field of the Invention

This invention relates to processes for preparing nitroaromatic glycosides, particularly nitroaromatic derivatives of maltotetraose, maltopentaose, and maltohexaose, useful as standard substrates for the assay of α-amylase in serum and other biological liquids.

2. Relation to the Prior Art

1. U.S. Pat. No. 3,879,263, issued Apr. 22, 1975 discloses the determination of the α-amylase content of biological samples by adding maltotetraose or maltopentaose to the sample at constant temperature and pH. The process allows rapid determination of α-amylase, and can be used to differentiate between saliva α-amylase and pancreas α-amylase. The latter produces glucose, whereas the former does not. The glucose produced may be estimated spectrophotometrically, e.g., by nicotinamide-adenine dinucleotide (reduced form) (NADH) absorption of 340 nm. Because this assay depends upon glucose, a glucose detecting reaction is necessary. Furthermore, if glucose is present in the sample, it must either be removed or compensated for. The compounds of the present invention differ from this in that 4-nitrophenol is released as the substance which can then be related to α-amylase. This makes the assay independent of the glucose detecting step.

2. A. P. Jansen and P. G. A. B. Wydeveld, *Nature*, 182, 525 (1958) postulate that α-(p-nitrophenyl)maltoside could be a substrate for an amylase assay. However, this paper shows that the authors never identified the active agent responsible for their observations. They reported: (1) Incubation of human urine or saliva samples with α-(p-nitrophenyl)maltoside at 37° for 16 hr produced 4-nitrophenol, identified spectrophotometrically by mixing the hydrolyzate with 0.02 N sodium hydroxide. (2) The hydrolysis was inhibited by protein precipitants such as 10% trichloroacetic acid and 0.5 N silver nitrate. (3) The hydrolysis was pH-dependent, being most effective at pH 5.9–7.0. They state that this was evidence for "the possible existence of an unidentified carbohydrase". α-(4-Nitrophenyl)maltoside is not believed to be useful for an amylase assay because the cleavage of this compound by α-amylase is extremely slow.

SUMMARY OF THE INVENTION

According to the present invention there is provided a process for preparing α and β nitroaromatic glycosides comprising:

(a) contacting an acetylated glycoside of the formula:

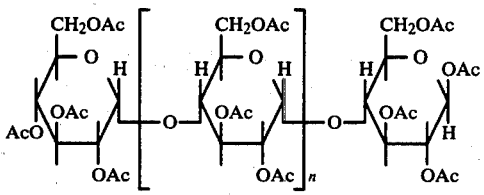

wherein Ac is an acetyl group, and n is an integer of 2, 3 or 4, with a phenol selected from the group consisting of

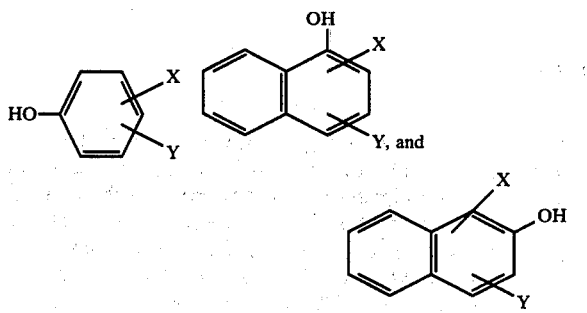

wherein X and Y are individually H, $NO_2$, halogen, alkyl of 1 to 4 carbon atoms, $OR'$ or $CO_2R'$ where $R'$ is an alkyl group of 1 to 6 carbon atoms, with the proviso that only one of X and Y is $NO_2$, in the presence of a catalyst at a temperature in the range of about 80°–120° C.;

(b) nitrating the product of (a) by contacting said product with:
 (i) nitric acid contained in a mixture of acetic acid and sulfuric acid, or
 (ii) a nitronium compound selected from nitronium tetrafluoroborate, nitronium hexafluorophosphate and nitronium, trifluoromethanesulfonate contained in dichloromethane, chloroform or 1,2-dichloroethane; and (c) deacetylating the product of (b) by contacting said product with:
 (i) a catalytic amount of an alkali metal lower alkoxide contained in the corresponding alcohol, or
 (ii) a solution of anhydrous ammonia or HCl in methanol.

The compounds of the invention are useful standard substrates for the assay of serum α-amylase in the study of pancreatic function.

DETAILED DESCRIPTION OF THE INVENTION

The nitroaromatic glycosides of the invention are derived from a series of oligomers and polymers of glucose which are α[1 → 4] linked. This series of glucosides has the general formula indicated below. The $G_n$ nomenclature is convenient shorthand for n α[1 → 4] linked glucose units.

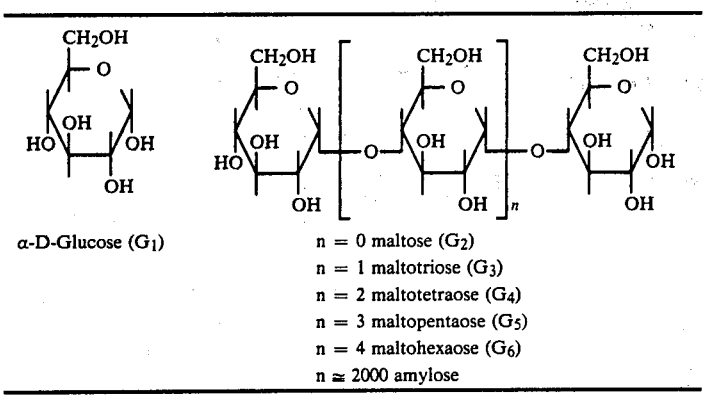

a-D-Glucose (G₁)  
n = 0 maltose (G₂)  
n = 1 maltotriose (G₃)  
n = 2 maltotetraose (G₄)  
n = 3 maltopentaose (G₅)  
n = 4 maltohexaose (G₆)  
n ≅ 2000 amylose For brevity in discussing the invention, trivial names and shorthand abbreviations will be used as shown in Table I. It is understood that these refer to the systematic names identified in Table I, the rules for which are given in "Naming and Indexing of Chemical Substances for Chemical Abstracts During the Ninth Collective Period (1972–1976)", Chemical Abstracts Service, Columbus, Ohio (1973).

Whistler and coworkers in *J. Amer. Chem. Soc.*, 76, 1671 (1954), 77, 1017, 5761 (1955) or Thomas John Pankratz in coassigned application Ser. No. 675,649, filed Apr. 9, 1976 now U.S. Pat. No. 4,039,383. The preferred nitroaromatic glycosides of G₄ and G₅ can be made from pure G₄ and G₅, prepared by chromatography of the hydrolyzate of amylose as described by W. Pigman, "*The Carbohydrates*", Academic Press, New York,

TABLE I
NOMENCLATURE OF GLUCOSE α[1→4] OLIGOSACCHARIDES

| Shorthand | Trivial Name | Systematic Name |
|---|---|---|
| G₁ | D-Glucose | D-Glucose |
| G₂ | Maltose | 4-0-α-D-glucopyranosyl-D-glucose |
| G₃ | Maltotriose | 0-α-D-glucopyranosyl-(1→4)-0-α-D-glucopyranosyl-(1→4)-D-glucose |
| G₄ | Maltotetraose | 0-α-D-glucopyranosyl-(1→4)-0-α-D-glucopyranosyl-(1→4)-0-α-D-glucopyranosyl-(1→4)-D-glucose |
| G₅ | Maltopentaose | 0-α-D-glucopyranosyl-(1→4)-0-α-D-glucopyranosyl-(1→4)-0-α-D-glucopyranosyl-(1→4)-0-α-D-glucopyranosyl-(1→4)-D-glucose |
| G₆ | Maltohexaose | 0-α-D-glucopyranosyl-(1→4)-0-α-D-glucopyranosyl-(1→4)-0-α-D-glucopyranosyl-(1→4)-0-α-D-glucopyranosyl-(1→4)-0-α-D-glucopyranosyl-(1→4)-D-glucose |
| G₄pNp | α-(4-Nitrophenyl)maltotetraoside | 4-Nitrophenyl-0-α-D-glucopyranosyl-(1→4)-0-α-D-glucopyranosyl-(1→4)-0-α-D-glucopyranosyl-(1→4)-α-D-glucopyranoside |
| G₅pNp | α-(4-Nitrophenyl)maltopentaoside | 4-Nitrophenyl-0-α-D-glucopyranosyl-(1→4)-0-α-D-glucopyranosyl-(1→4)-0-α-D-glucopyranosyl-(1→4)-0-α-D-glucopyranosyl-(1→4)-α-D-glucopyranoside |
| G₃(Ac)₁₀ | Decaacetylmaltotriosyl | 2,3,6,2',3',6',2'',3'',4'',6''-Decaacetyl-0-α-D-glucopyranosyl-(1→4)-0-α-D-glucopyranosyl-(1→4)-0-α-D-glucopyranosyl |

The glucose oligomer starting materials, i.e., maltotetraose, maltopentaose and maltohexaose can be prepared by the procedure described by either R. L. 1957, pages 678–9. Scheme I illustrates a procedure for preparing the preferred compounds of the invention. The details of each step will be described hereinafter.

SCHEME I: SYNTHETIC SCHEME

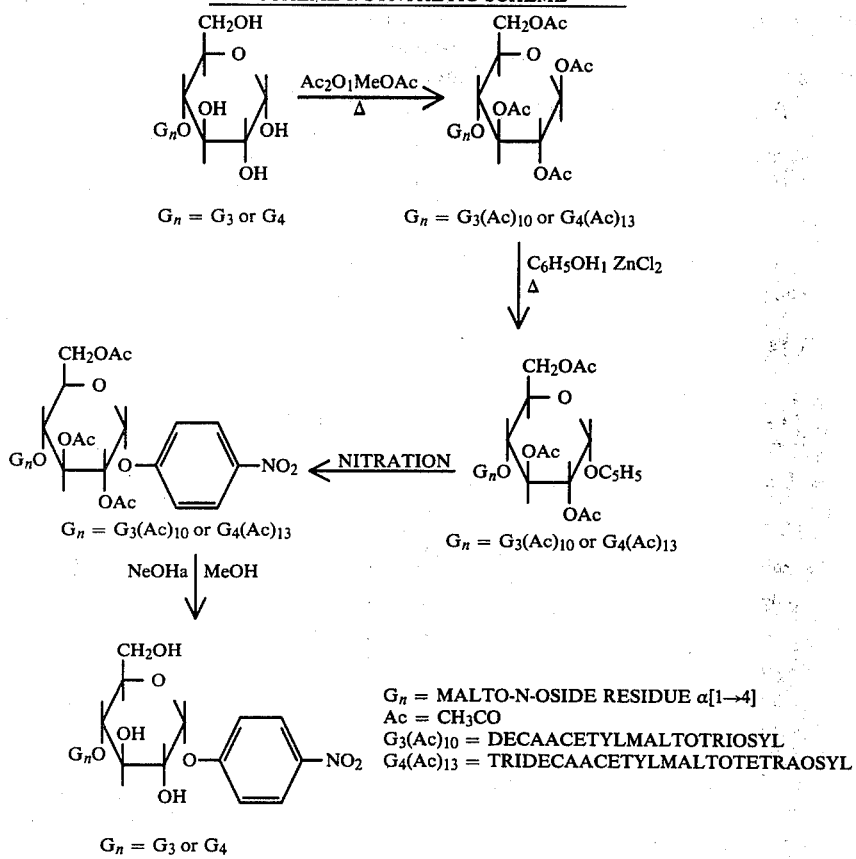

The above reaction scheme tends to maximize formation of α-(4-nitrophenyl)glycosides (as shown), but substantial amounts, for example, 20% or more, of the β-isomer are also produced.

The details of each step of the procedure for preparing the compounds of the invention are as follows:

ACETYLATION REACTION

The acetylation of glucose oligomers with a mixture of acetic anhydride and anhydrous sodium acetate at elevated temperatures is known (W. J. Whelan and P. J. P. Roberts, *J. Chem. Soc.*, 1298 (1953), W. J. Whelan, J. M. Bailey, and P. J. P. Roberts, *J. Chem. Soc.*, 1293 (1953), A. Thompson and M. L. Wolfrom, *J. Amer. Chem. Soc.*, 74, 3612 (1954), M. L. Wolfrom, L. W. Georges, A. Thompson, and I. L. Miller, *J. Amer. Chem. Soc.*, 71, 2875 (1949)) to give the completely acetylated derivatives with the acetoxy substituent on the anomeric carbon being mostly in the β-configuration. On the other hand replacement of the anhydrous sodium acetate with zinc chloride or acids favors the production of compounds where the substituent on the anomeric carbon is in the α-configuration (W. Pigman, loc. cit. p. 140–142). In either case a mixture of the α and β isomers is obtained. The acetylation is conducted in acetic anhydride as the solvent and reactant, the amount of acetic anhydride being from 5 to 50 times the weight of $G_4$ or $G_5$. The preferred amount is 5 to 10 times the weight of $G_4$ or $G_5$ in order to provide sufficient reagent, to keep the reactants in solution, and to permit isolation of the product when the reaction mixture is poured into water. The amount of anhydrous sodium acetate used may be from 1 to 10 molar equivalents per molar equivalent of $G_4$ or $G_5$, preferably from 5 to 6 molar equivalents.

The temperature of the reaction can be from 100° C. to 140° C., the reflux temperature of acetic anhydride, and is preferably between 110° C. and 120° C. Below 100° C., the acetylation proceeds very slowly and incompletely, and above 140° (e.g., in a pressure vessel), the reaction is very vigorous and gives a dark-colored product.

The reaction time can be from 1 to 6 hours, and is preferably about 2 hours. Prolonged heating at elevated temperature also gives a dark-colored product. The onset of the reaction is signalled by the reaction mixture becoming a homogeneous solution and by the reaction becoming mildly exothermic.

The completely acetylated product is isolated by pouring the cooled reaction mixture into ice-water from five to twenty times the volume of acetic anhydride taken, stirring the mixture vigorously for a few minutes, and then allowing it to stand at 0°–5° C. for at least 24 hours. The solid product, whose crystallization can be improved and accelerated by seeding, if desired, is filtered, air-dried, and recrystallized from a suitable solvent such as ethanol or methanol.

The identity of this and other intermediate products is established by the usual spectral properties and analyses. The stereochemistry of the anomeric carbon is readily established by proton nuclear magnetic resonance spectroscopy ($^1$H nmr), especially at high frequencies such as 220 MHz, and by optical rotation studies, if desired. In the nmr of aldopyranose acetates, an anomeric proton in the α-configuration ($H_{1\alpha}$) can be distinguished from an anomeric proton in the β-configuration (H$_{1\beta}$). In the nmr of aldopyranose acetates, an anomeric proton in the α-configuration (H$_{1\alpha}$) has a chemical shift (δ) near 5.75 ppm downfield of internal tetramethylsilane, and the signal appears as a doublet with an axial-axial coupling constant (J) of 7–9 Hz. An anomeric proton in the β-configuration (H$_{1\beta}$) gives a signal 0.2–0.65 ppm downfield of this position, also as a doublet with an axial-equatorial or equatorial-equatorial coupling constant of 3–4 Hz (See, for example, L. M. Jackman, "Applications of NMR Spectroscopy in Organic Chemistry", Pergamon Press (London), (1959), pp 86, 116).

ACETATE DISPLACEMENT REACTION

The displacement of the anomeric acetate group in a completely acetylated sugar occurs more readily than that of the other acetate groups; this is a useful property for synthetic purposes because it permits preferential reaction at this position. For example, when tetradecaacetylmaltotetraoside or heptadecaacetylmaltopentaoside is stirred with phenol and anhydrous zinc chloride (ZnCl$_2$) at elevated temperatures, the anomeric β-acetoxy group is replaced for the most part by an α-phenoxy group. While at least one molar equivalent of phenol is required per molar equivalent of acetyl compound to satisfy the stoichiometry of the reaction, the reaction can be carried out with from 3 to 20 molar equivalents of phenol, preferably with 4 to 8 molar equivalents to provide sufficient material to form a homogeneous solution. The amount of zinc chloride can be from 0.25 to 5 molar equivalents per molar equivalent of acetyl compound, and is preferably in the range of 0.5 to 1.5 molar equivalents. This reaction can be carried out in the temperature range of from 80° C. to 120° C., with temperatures in the range of 100° C. to 110° C. being preferred, for the same reasons given above in the first step of the process. The reaction time can be from 0.25 to 6 hours, with 1 to 3 hours usually being sufficient. Zinc chloride dissolved in a mixture of acetic acid:acetic anhydride (e.g., a 95:5 volume mixture) is a useful modification of the above solvent and catalyst system for the introduction of the α-phenoxy group.

The anhydrous zinc chloride catalyst may be replaced by acids such as p-toluenesulfonic acid and by other anhydrous covalent metal chlorides such as titanium (IV) chloride (TiCl$_4$), tin (IV) chloride (SnCl$_4$), and iron (III) chloride (FeCl$_3$).

The displacement reaction proceeds without solvent because the low melting point of phenol (43° C.) ensures that when excess phenol is taken to drive the reaction to completion, the mixture remains as a homogeneous solution at the reaction temperature. Similar reactions are also expected to succeed when excess amounts of phenols which are liquid at the reaction temperature are used both as the solvent and reactant, for example, 2-cresol (mp 30° C.), 3-cresol (mp 11° C.), 4-cresol (mp 35° C.), 2-chlorophenol (mp 8° C.), 3-chlorophenol (mp 29° C.), 4-chlorophenol (mp 37° C.), 4-bromophenol (mp 64° C.), 2-nitrophenol (mp 45° C.), 2-methoxyphenol (guaiacol, mp 32° C.), 4-methoxyphenol (mp 53° C.), 2-methyl-5-isopropylphenol (carvacrol, mp 1° C.), 2-isopropyl-5-methylphenol (thymol, mp 51° C.), and methyl salicylate (mp −8° C.). With higher melting phenols, as well as those specified above, it is also possible to do the reaction in a solvent such as benzene (bp 80° C.), toluene (bp 110° C.) or heptane (bp 98° C.). With higher-melting phenols such as 3-nitrophenol (mp 96° C.), 4-nitrophenol (mp 114° C.), 2,4-dinitrophenol (mp 113° C.), 1-naphthol (mp 94° C.), and 2-naphthol (mp 122° C.), the solvent method renders the mixture homogeneous and prevents charring of the acetyl derivative. The solvent may also be one of the above-mentioned catalysts which is a liquid at the reaction temperature, such as titanium (IV) chloride (bp 136° C.) or tin (IV) chloride (bp 114° C.). If desired, the product of the reaction with the phenol can be reacetylated by the procedure of the first step to protect any free hydroxyl groups which may have arisen by deacetylation side reactions during the introduction of the phenoxy group.

NITRATION REACTION

While the direct use of 4-nitrophenol to prepare 4-nitrophenylglycosides has been described and may be used (T. D. Audichya, T. R. Ingle, and J. L. Bose, *Indian J. Chem.*, 9, 315 (1971), A. P. Jansen and P. G. A. B. Wydeveld, loc. cit.), the described process shown in Scheme I to (4-nitrophenyl)tridecaacetylmaltotetraoside and (4-nitrophenyl)hexadecaacetyl maltopentaoside is preferred for ease of operation. The nitration can be accomplished either in a mixture of acetic and sulfuric acids with nitric acid, or in dichloromethane with a nitronium compound such as nitronium tetrafluoroborate (NO$_2$+BF$_4$−), nitronium hexafluorophosphate (NO$_2$+PF$_6$−) or nitronium trifluoromethanesulfonate (No$_2$+CF$_3$SO$_3$−). These are all described in L. F. Fieser and M. Fieser, *Reagents for Organic Synthesis* 5, 477 (1975), Wiley-Interscience, New York. Nitronium tetrafluoroborate is preferred and will be used to describe this aspect of the procedure. In the first procedure, a solution of the phenyl acetylated glycoside in a mixture of sulfuric and acetic acids at 0° C. to 25° C. is treated with a 5 to 30-fold molar excess of 70% nitric acid dissolved in acetic acid. The preferred amount of nitric acid is from 10 to 20 molar equivalents per molar equivalent of acetyl derivative. The reaction temperature is between 0° C. and 25° C. (preferably about 0° C.) to minimize further nitration of the aromatic ring and cleavage of ester and glycosidic linkages. While the reaction time can be from 1 to 10 hours (about 4 hours preferred), the nitration should be allowed to occur as completely as possible without the formation of the above-mentioned further products. The nitration of the aromatic glycoside acetates produced from the phenols listed above for the displacement reaction follows the usual ortho-para substitution pattern with the para-position being favored unless it is blocked by another group, as in the 4-cresyl derivative. The amount of metasubstitution is negligible.

In the nitronium tetrafluoroborate procedure, the preferred reaction time is from 0.25 to 1 hour and the preferred reaction temperature is about 25° C. The molar proportion of nitronium tetrafluoroborate to acetylated glycoside can be between 1 and 20:1, with 10 to 1 as the preferred ratio to ensure complete introduction of 1 nitro group. In addition to the preferred solvent dichloromethane, chloroform and 1,2-dichloroethane can be used. The nitronium tetrafluoroborate procedure is preferred for its ease of operation.

The resulting nitrated product of the first procedure can be isolated from the mixture of nitric, acetic and sulfuric acids by pouring the reaction mixture into water (usually about 5 to 20 times its volume) and either filtering the crude product, or extracting it with chloroform. In the nitronium tetrafluoroborate process, the dichloromethane solution is added to cold saturated sodium chloride solution, dried over sodium sulfate, and evaporated to leave the crude glycoside.

DEACETYLATION REACTION

The selective removal of 0-acetyl groups from an acetylated polyol derivative is preferably accomplished either with a catalytic amount of sodium methoxide (usually 0.01–0.1 molar equivalent) in methanol, or by a solution of anhydrous ammonia in methanol. In addition to the preferred sodium methoxide, other alkali metal lower alkoxides such as potassium methoxide, sodium and potassium ethoxide and potassium t-butoxide can be used. These deacetylation reactions occur readily at temperatures of 0°–25° C. within 12 to 24 hours. The deacetylated product is isolated by evaporation of the methanol, freed of inorganic ions (if desired) by passage through an acidic ion-exchange column, and recrystallized from a suitable solvent such as methanol or ethanol. An alternative deacetylation procedure uses a 3% solution of hydrogen chloride in methanol (L. F. and M. Fieser, "Reagents for Organic Syntheses", Wiley, N.Y., 1967, p. 11) at temperatures of 0°–25° C. for periods of 4–24 hours. This is especially useful for dinitro compounds.

An alternative synthesis is to use one of the phenols to displace the halogen from tridecaacetylmaltotriosyl or hexadecaacetylmaltopentaosyl chloride or bromide of the following structure.

The halogen atom is either displaced with phenol or a substituted phenol in the presence of a halogen acceptor such as silver (I) oxide ($Ag_2O$), silver (I) carbonate ($Ag_2CO_3$), mercury (II) acetate ($Hg(CH_3COO)_2$), or with iron (III) chloride (Koenigs-Knorr reaction), or with the sodium or potassium salt of the phenol (W. Pigman, loc. cit., p. 194–198). The rest of the synthesis is the same as described above.

The progress of any of the above reactions can be followed by thin-layer chromatography (TLC) on silica gel in a suitable solvent system, and by nmr spectroscopy. The purity of the products of the reactions can be determined by high-performance liquid chromatography (HPLC), by polarimetry, and by ultraviolet and high-frequency (220 MHz) nmr spectroscopy.

It has been found that the nitroaromatic glycosides of the invention are useful substrates for serum $\alpha$-amylase assay. The assay process is illustrated in Scheme II for the preferred compounds of the invention, isomeric $\alpha$- and $\beta$-(4-nitrophenyl)maltotetraosides and $\alpha$- and $\beta$-(4-nitrophenyl)-maltopentaosides. Serum $\alpha$-amylase converts these compounds to a mixture of $G_2$ or $G_3$ and isomeric (4-nitrophenyl)maltosides. The latter are then hydrolyzed to glucose and 4-nitrophenol by $\alpha$-maltase or a mixture of $\alpha$-maltase and $\beta$-maltase. $\alpha$-Maltase is sensitive and specific for cleaving the $\alpha$-nitroaromatic maltoside linkage, while $\beta$-maltase is similarly sensitive and specific for cleaving the $\beta$-nitroaromatic maltoside

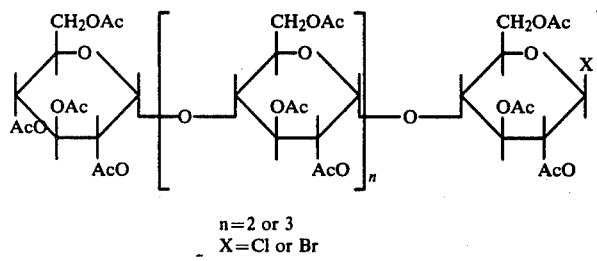

n=2 or 3
X=Cl or Br

These halides are prepared either by treatment of the completely acetylated oligosaccharide with anhydrous hydrogen halide, solutions of hydrogen halide in mixtures of acetic anhydride and acetic acid, solutions of aluminum chloride and phosphorus pentachloride or of titanium tetrachloride in chloroform, or from the oligosaccharide itself by treatment with acetyl chloride (W. Pigman, loc, cit., p. 150–151).

link. Thus, by employing a mixture of both maltase enzymes, mixed isomeric $\alpha$- and $\beta$-nitroaromatic glycosides of the invention may be completely utilized, resulting in maximum assay sensitivity. Treatment of the hydrolzate with dilute alkali produces the 4-nitrophenolate anion which is spectroscopically identifiable and distinguishable from any unreacted glycoside, and which can be related to serum $\alpha$-amylase levels.

SCHEME II: SERUM α-AMYLASE ASSAY

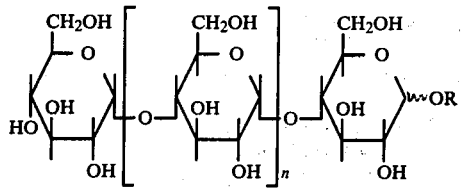

$\gamma_{max}$ 290–305nm

R = 4-O$_2$NC$_6$H$_4$  n = 2  α and β-(4-NITROPHENYL)MALTOTETRAOSIDE
n = 3  α and β-(NITROPHENYL)MALTOPENTAOSIDE

↓ α-ANYLASE

G$_2$ or G$_3$ +

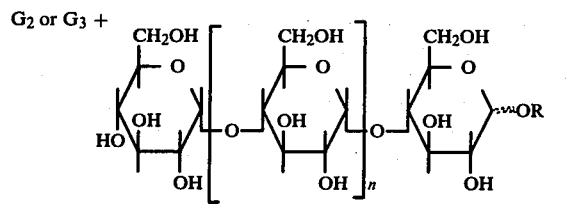

R = 4-O$_2$NC$_6$H$_4$  n = 0  α and β-(4-NITROPHENYL) MALTOSIDE

↓ α-MALTASE 4 or 5 G$_1$ + 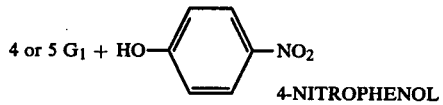

4-NITROPHENOL

↓ OH$^-$

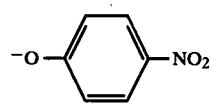

4-NITROPHENOLATE ANION  $\gamma_{max}$ 410 nm

The nitroaromatic glycosides of the invention have the following advantages in the assay of serum α-amlyase. In U.S. Pat. No. 3,879,263, serum α-amylase levels are related to the glucose produced from G$_4$ or G$_5$. Consequently, serum glucose must be removed chromatographically from the sample before assay, requiring the expenditure of sample preparation time and extra apparatus. By using compounds of the present invention, serum α-amylase levels are related to the nitrophenols produced from the nitroaromatic glycosides of G$_4$, G$_5$ or G$_6$ which are independent of serum glucose levels. Not only does this also do away with the chromatography system for removing serum glucose, but it also simplifies the detection system by replacing the hexakinase-ATP-NADP unit with dilute alkali, (ATP-NADP is adenosine triphosphate and nicotinamide-adenine dinucleotide phosphate).

EMBODIMENTS OF THE INVENTION

The following illustrative examples demonstrate ways of carrying out the invention. All parts and percentages are by weight, and all temperatures are Centigrade unless otherwise stated. Proton nuclear magnetic resonance ($^1$H nmr) chemical shifts are in parts per million from internal tetramethylsilane in chloroform-d (CDCl$_3$) unless otherwise stated; qualitative $^1$H nmr results were obtained at 60 MHz, and more accurate measurements were made at 220 MHz. Thin layer chromatograms (TLC) were run on silica gel using 250 μm plates for analytical work and 2 mm plates for preparative work. High performance liquid chromatograms (HPLC) were run on a Du Pont 830 instrument for analytical work, and on a Du Pont 841 instrument for preparative work.

EXAMPLE 1

(A) Preparation of Maltotetraose β-Tetradecaacetate

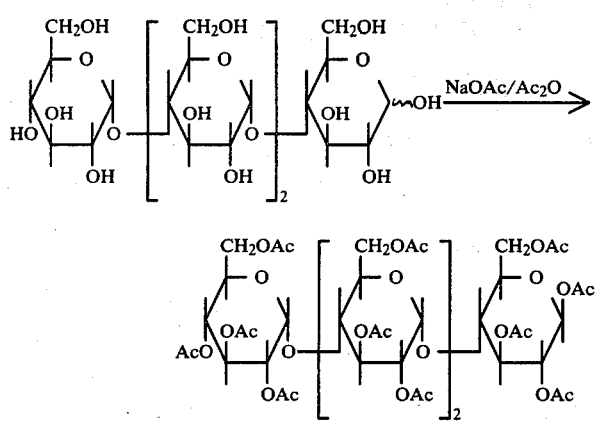

A mixture of maltotetraose of analytically confirmed structure (10.0 g, 15.0 mmole), anhydrous sodium acetate (10.0 g, 0.15 mole) and acetic anhydride (50 ml) was stirred at 100° for 2 hours, then it was poured into 300 ml of ice water. After 48 hr at 5°, the colorless crystalline mass was filtered and air-dried, yield 20.96 g of crude material. This was recrystallized from methanol (40 ml), recovery 18.18 g (14.49 mmole, 96%) of crystalline maltotetraose β-tetradecaacetate in two crops of 2.98 g and 15.20 g. The first crop material had mp 124°-126° and its structure was confirmed by: $\nu_{max}$ (CHCl$_3$), 1750, 1370, 1230 and 1030 cm$^{-1}$; $\lambda_{max}$(EtOH) 210 nm ($\epsilon$ 740); $[\alpha]_D^{25°}$ + 104° (c 1.03 CHCl$_3$); $^1$H nmr (220 MHz), $\delta$ 5.76 (d J = 7) (H$_{1\alpha}$), 5.43-5.25 (several groups of multiplets) 27H (OCH, OCH$_2$), and 2.19-2.00 (series of singlets) 42H (COCH$_3$);

Anal. Calcd. for C$_{52}$H$_{70}$O$_{35}$: C, 49.76; H, 5.62. Found: C, 49.08, 49.24; H, 5.76, 5.73.

In several further experiments up to twice the above scale, the yield of product was from 72–77% after recrystallization, and the mp was from 122° to 128°.

(B) Preparation of α- and β-Phenyltridecaacetylmaltotetraosides

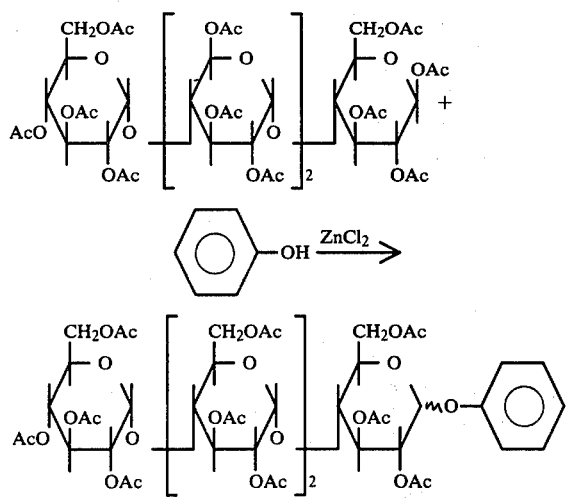

A mixture of maltotetraose β-tetradecaacetate from part (A) (11.0 g, 8.77 mmole), phenol (8.0 g, 85 mmole) and anhydrous zinc chloride (2.0 g, 14 mmole) was heated gently until it became fluid, and it was then stirred mechanically at 100° for 3 hr. The mixture was diluted with water and benzene and separated. The benzene layer was extracted in turn with 3 × 50 ml of 5% sodium hydroxide, 2 × 50 ml of saturated aqueous sodium chloride, dried, and evaporated to give 10.09 g (7.8 mmole, 89%) of crude phenyl derivative as a yellow crystalline solid. This material was purified by preparative thin layer and high performance liquid chromatography as follows:

A total amount of 3.06 g of crude phenyl derivative was loaded onto 14 2-mm preparative TLC plates and developed 3 times with a mixture of 95:5 benzene:methanol. The R$_f$0.13–0.27 band was extracted with chloroform and methanol to give 0.90 g (29%) of material which was recrystallized from ethanol, recovery 0.58 g of a mixture of α- and β-phenyltridecaacetylmaltotetraosides. Analytical HPLC (polar silicone microspheres) showed product with retention time 8.99 min and a minor impurity (2.4%) at 8.23 min. The structure of the crystalline phenyltridecaacetylmaltotetraoside was confirmed by: $\nu_{max}$(CHCl$_3$) 1745, 1595, 1585, 1365, 1225, and 1030 cm$^{-1}$; $\lambda_{max}$(EtOH) 273 nm ($\epsilon$ 800), 266 (960), 260 (730), 210 (7860); $[\alpha]_D^{25°}$ + 132° (c 1.00 CHCl$_3$); $^1$H nmr (220 MHz), $\delta$7.37-7.25 (m) 2H, 7.14-6.95 (m) 3H (C$_6$H$_5$), 5.00-3.86 (m) 28H (OCH, OCH$_2$), and 2.19-1.97 ppm (series of singlets), 39H (COCH$_3$);

Anal. Calcd. for C$_{56}$H$_{72}$O$_{34}$: C, 52.17; H, 5.63. Found: C, 51.44, 51.94, 51.60; H, 5.35, 5.60, 5.39.

A total amount of 4.25 g of the crude phenyl derivative was also purified by preparative HPLC on a 1 m × 23 mm Spherosil (44–50) column eluted with a mixture of 1:1 pentane:dioxane (containing 1.5% water) to give 1.07 g (25% recovery) of colorless crystalline phenyltridecaacetylmaltotetraoside, mp 82°-83°, identical by spectral and chromatographic data with the material purified by TLC. Analytical HPLC showed this sample to be 99.7% pure, (C) Preparation of α- and β-Phenyltridecaacetylmaltotetraosides (Alternate Method)

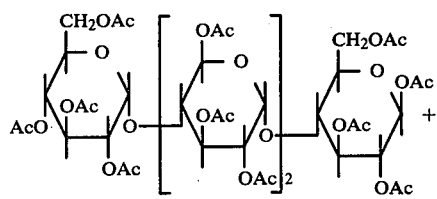

(D) Preparation of α- and β-(4-Nitrophenyl)tridecaacetylmaltotetraoside (Nitric Acid Method)

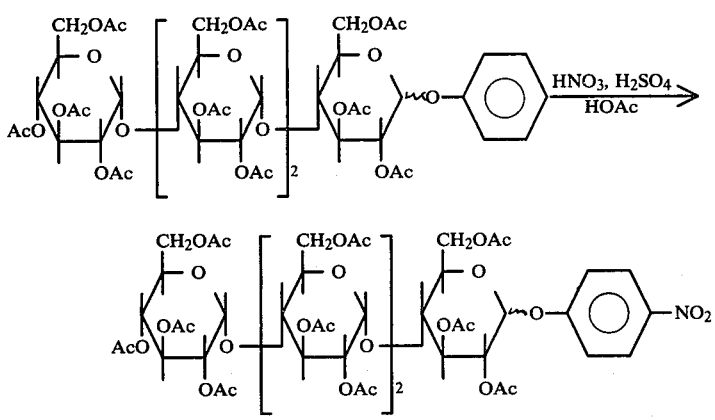

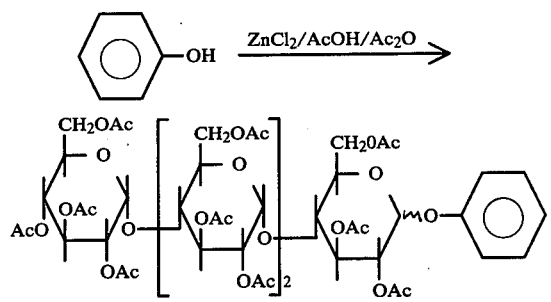

Maltotetraose β-tetradecaacetate (2.75 g, 2.19 mmole) and phenol (2.27 g, 24.2 mmole) were mixed in a 3-neck flask under nitrogen. Zinc chloride (0.55 g) dissolved in 2.0 ml of a mixture of 95:5 acetic acid:acetic anhydride was added, and the reaction mixture was slowly warmed. When the mixture became homogeneous (temperature ca. 45°), the internal pressure was gradually lowered to 23 mm and the reaction mixture was stirred at 100° for 2.5 hr. The material was transferred to a separatory funnel using warm benzene (200 ml), and the cooled mixture was washed twice with 18% aqueous sodium chloride, twice with 2.5% sodium hydroxide (50 ml) and twice with saturated sodium chloride (30 ml). The organic layer was dried over sodium sulfate, evaporated, and the residue treated with anhydrous sodium acetate (3.0 g) and acetic anhydride (15 ml). The resulting mixture was heated at 120° for 1.0 hr, cooled, and treated with ice-water (200 ml). This procedure reacetylates any unprotected hydroxyl groups which arise from the phenol procedure. The solid which formed upon standing at 0° was filtered and dried, yield 2.85 g. This material was chromatographed on silica gel (Mallinckrodt SilicAR ® CC-7). Elution with a mixture of 97:3 benzene:methanol gave a total of 2.07 g (71%) of pure phenyltridecaacetylmaltotetraoside after recrystallization from ethanol. This material had mp 112°–117° and its structure was confirmed by: $[\alpha]_D^{25°}$ + 135° (c 1.0 CHCl$_3$), $^1$H nmr (220 MHz) δ 7.38-6.96 (m) 5H (C$_6$H$_5$), 5.77 (dd J = 9.5 Hz) (H$_{1\alpha}$), and 5.61 (d J = 4 Hz) (H$_{1\beta}$) 1H, 5.45-3.82 (series of multiplets) 27H (OCH, OCH$_2$), and 2.24-1.95 ppm (series of singlets) 39H (COCH$_3$); integration was consistent with a 75:25 mixture of α:β phenyltridecaacetylmaltotetraosides.

A mixture of acetic acid (2.0 ml), acetic anhydride (1.0 ml) and preparative TLC-purified α- and β-phenyltridecaacetylmaltotetraoside mixture from Part (B) (0.38 g, 0.29 mmole) was cooled to 0° and treated with a mixture of sulfuric acid (1.0 g) and acetic acid (2.0 g), and then with a mixture of 70% nitric acid (0.5 g) and acetic acid (1.0 ml). The mixture was stirred at 25° for 4 hr, poured into ice water (25 ml), and filtered to give 0.40 g of almost colorless solid. This sample was approximately 50% 4-nitrophenyl derivative as indicated by $\lambda_{max}$ (EtOH) 290 nm (ε 3100).

The reaction was repeated on a larger scale (5 g of crude phenyltridecaacetylmaltotetraoside) to give 4.35 g (84%) of crude nitro compound which was chromatographed on silica gel (200 g) (Mallinckrodt SilicAR ® CC-7). The product (2.27 g recovered), eluted with 4% methanol in benzene was also approximately 50% pure.

A 2.6-g sample of crude precipitated nitro compound was purified by preparative HPLC separation using a 2 m × 2.3 cm Spherosil (44–50) column eluted with a mixture of 1:1 pentane:dioxan (containing 1.5% water). The fractions were examined by TLC and UV, and from the middle cuts, 0.2557 g (0.19 mole, 8%) of pure α- and β-(4-nitrophenyl)tridecaacetylmaltotetraoside was obtained. After recrystallization from ethanol (5 ml) this material had mp 112°–114°. The structure of the material was confirmed by $\nu_{max}$ (CHCl$_3$) 1745, 1580, 1520, 1420, 1370 and 1220 cm$^{-1}$; $\lambda_{max}$(EtOH) 290 nm (ε 7180); $[\alpha]_D^{25°}$ + 156° (c 0.525 CHCl$_3$); $^1$H nmr (220 MHz), δ 8.26 (d J = 8) and 7.26 (d J = 8) 4H (C$_6$H$_4$), 5.75 (m) 1H (H$_{1\alpha}$ and H$_{1\beta}$), 5.52-3.95 (series of multiplets) 27H (OCH, OCH$_2$), and 2.25-2.01 ppm (series of singlets) 39H (COCH$_3$);

Anal. Calcd. for C$_{56}$H$_{71}$NO$_{36}$: C, 50.41; H, 5.36. Found: C, 49.95; H, 5.54.

(E) α- and β-(4-Nitrophenyl)tridecaacetylmaltotetraoside

(F) Preparation of α- and β-(4-Nitrophenyl)maltotetraoside

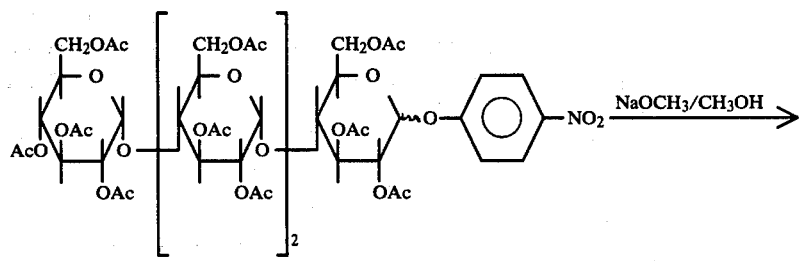

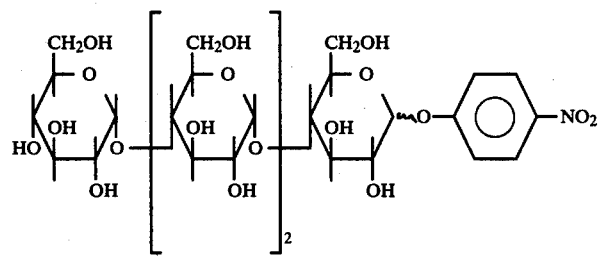

(Nitronium Tetrafluoroborate Method)

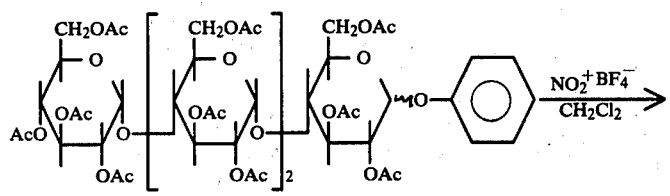

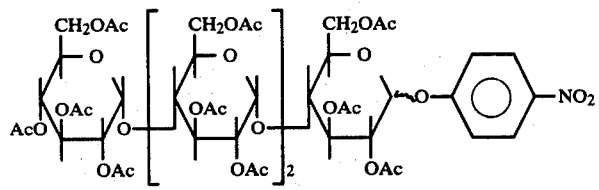

A slurry of nitronium tetrafluoroborate (1.91 g, 14.5 mmole) in dry methylene chloride (8 ml) was treated with a solution of phenyltridecaacetylmaltotetraoside from part (C) (1.24 g, 0.96 mmole) in dichloromethane (10 ml), and the resulting mixture stirred for 20 min under an argon atmosphere. The mixture was added to ice water (60 ml), separated, and washed with cold saturated aqueous sodium chloride. The organic portion was dried over magnesium sulfate and evaporated under reduced pressure to provide a yellow glassy solid (1.30 g) of α- and β-(4-nitrophenyl)tridecaacetylmaltotetraoside product. Half of this product was recrystallized from ethanol to provide a cream-colored solid, 0.48 g (75%), mp 116°-119°. The structure of the product was confirmed by: $^1$H nmr (220 MHz), δ 7.75 (AA',BB') 4H ($C_6H_4$), 5.75 (d J = 4Hz) ($H_{1\beta}$) and 5.81-3.86 (series of multiplets) 28H ($H_{1\alpha}$, OCH, $OCH_2$), and 2.25-1.95 (series of singlets) 39H ($COCH_3$); $\lambda_{max}$ (EtOH) 288 nm (ε 5840); $[\alpha]_D^{25°}$ + 152° (c 0.5 $CHCl_3$).

A mixture of column-chromatographed 4-(nitrophenyl)-tridecaacetylmaltotetraoside from part (D) (6.76 g, 5.1 mmole), methanol (50 ml) and sodium methoxide (50 mg) was left at 25° overnight. The mixture was filtered to remove a small amount of yellow solid, and the filtrate was evaporated to leave 3.17 g (4.02 mmole, 79%) of yellow solid. Three grams of this sample were purified by preparative TLC on 11 plates by development in a mixture of 3:3.5:0.5 chloroform:acetic acid:water. Material (0.5027 g) from the $R_f$ 0.16-0.29 band was a mixture of α- and β-(4-nitrophenyl)maltotetraoside, approximately 50% pure by UV. The product was a yellow solid with mp 68°-70° and its structure was confirmed by: $\nu_{max}$ (Nujol) 3300 and 1020 cm$^{-1}$; $\lambda_{max}$ ($H_2O$) 305 nm (ε 3740); $[\alpha]_D^{25°}$ + 104° (c 1.06 $H_2O$); $^1$H nmr (220 MHz), δ 8.25 (d J = 10) and 7.35 (d J = 10) ($C_6H_4$), 7.91 (t J = 7) and 7.70 (t J = 7) (other aromatic material), 5.88-5.79 (m) ($H_{1\alpha}$ and $H_{1\beta}$), 5.30 (m) (OCHO), 4.98 (s) (HOD), and 4.02-3.48 ppm (m) (OCH,$OCH_2$).

(G) (4-Nitrophenyl)maltotetraoside (Alternate Method)

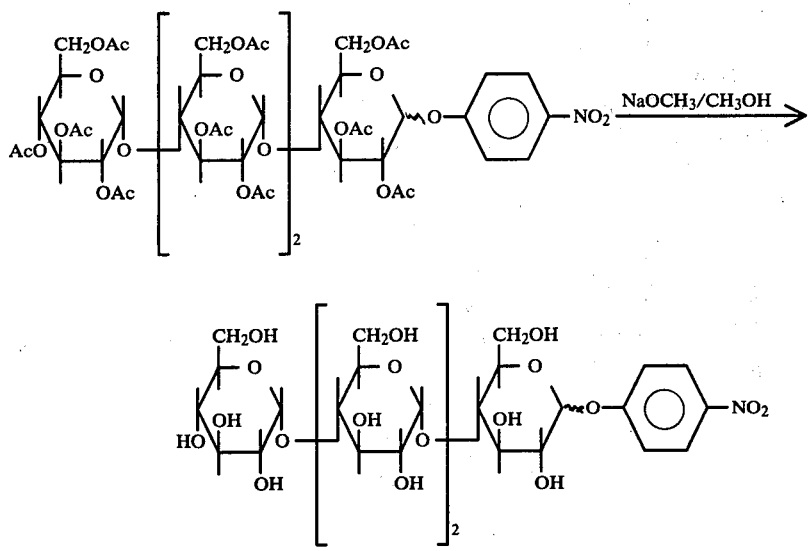

A mixture of (4-nitrophenyl)tridecaacetylmaltotetraoside from part (E) (250 mg, 0.19 mmole) in methanol (2.5 ml) was treated with a solution of sodium methoxide in methanol (3.3 ml of 7.8 × 10$^{-3}$ M solution) and was stirred for 17 hr at room temperature. Solvent was removed under reduced pressure and the residue, dissolved in a minimal volume of methanol (2 ml), was added dropwise to ether (40 ml). The resulting yellow powder was separated, dissolved in methanol, and passed through a 2.5 × 20 cm column of Sephadex® LH-20 using methanol as eluant. There was obtained 134 mg (90%) of solid product which was re-chromatographed to provide a center cut (90 mg, 60%) having its structure confirmed by: $\lambda_{max}$ (H$_2$O) 303 nm ($\epsilon$ 6350), 217 ($\epsilon$ 5000); $^1$H nmr (220 MHz), $\delta$ (CD$_3$OD) 7.77 (AA',BB', J$_{AB}$ = 9.5 Hz) 4H (C$_6$H$_4$), 5.69 (d J = 4Hz) 1H (H$_{1\beta}$), 5.27-5.09 (m) 3H(OCHO), 4.87 (s) 13H (HOD), 4.20-4.05 (m) (minor impurity), and 4.01-3.40 ppm (m) (OCH, OCH$_2$).

(H) (4-Nitrophenyl)maltotetraoside (Alternate Method)

The procedure described in part (G) was used to prepare a crude sample of (4-nitrophenyl)maltotetraoside, $\lambda_{max}$ (H$_2$O) 302 nm ($\epsilon$ 5900), 217 (4650); [$\alpha$]$_D^{25}$ + 158° (c 1.1, CH$_3$OH). A portion of this sample was purified by fractionation on a Waters Associates $\mu$ Bondapak/Carbohydrate column eluting with an 87:13 mixture of acetonitrile:water. The purified major component of the sample obtained after freeze drying exhibited $\lambda_{max}$ (H$_2$O) 302 nm ($\epsilon$ 9425), 220 (6500).

EXAMPLE 2

(A) Preparation of Maltopentaose $\beta$-Heptadecaacetate

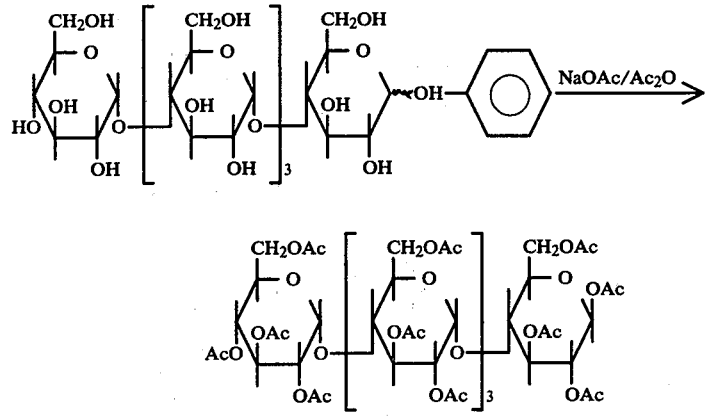

A mixture of maltopentaose (2.00 g, 2,41 mmole), sodium acetate (2.0 g, 30 mmole), and acetic anhydride (20 ml) was heated at 130° for 2.0 hr. The cooled mixture was added to ice (75 g) and stored at 0°. The resulting solid was pulverized and filtered to give an off-white solid (3.35 g, 90%) which was recrystallized from ethanol (40 ml) to provide maltopentaose $\beta$-heptadecaacetate, 3.16 g (85%), mp 117°-120°; whose structure was confirmed by: [$\alpha$]$_D^{25}$ + 122° (c 0.7, CHCl$_3$); $^1$H nmr (60 MHz) $\delta$ 5.85-3.78 (m) 35H (OCH, OCH$_2$), and 2.34-1.83 ppm (series of singlets) 51H (COCH$_3$); $^1$H nmr (220 MHz) $\delta$ 5.76 ppm (d J = 8 Hz) 1H (H$_{1\alpha}$);

Anal. Calcd. for C$_{64}$H$_{86}$O$_{43}$: C, 49.80; H, 5.62. Found: C, 49.11, 49.28; H, 5.54, 5.71.

(B) Preparation of α- and β-Phenylhexadecaacetylmaltopentaoside

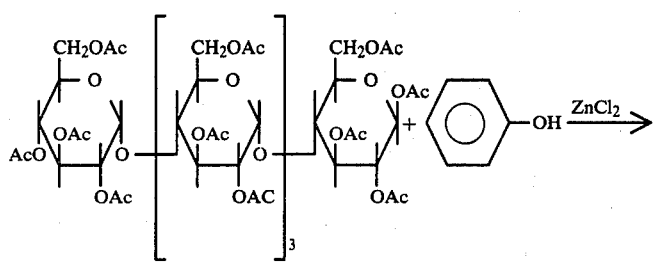

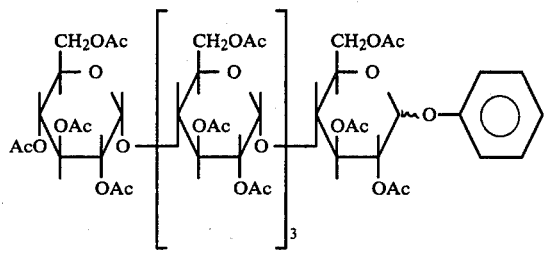

A mixture of maltopentaose β-heptadecaacetate from part (A) (3.00 g, 1.95 mmole), phenol (1.95 g, 20.8 mmole) and anhydrous zinc chloride (0.46 g, 3.38 mmole) was heated at 100° for 3 hr under an argon atmosphere. The cooled mixture was taken up in dichloromethane (200 ml) and washed with water (2 × 30 ml), 5% sodium hydroxide (2 × 25 ml), and brine (2 × 25 ml). The organic layer was dried over magnesium sulfate and concentrated under reduced pressure to give a yellow powder which was treated with sodium acetate (3.0 g) and acetic anhydride (15 ml) and then heated at 125° for 2.0 hr in order to reaacetylate any free hydroxyl groups. The cooled mixture was added to ice (125 g) and stored at 5°. The resulting α- and β-phenylhexadecaacetylmaltopentaoside solid product was pulverized, separated and air-dried to give 2.45 g of an off-white powder. This material was chromatographed on silica gel (150 g) eluting with a mixture of 97:3 benzene:methanol. The $^1$H nmr (220 MHz) of the residue from a center cut exhibited δ 7.38-7.27 (m) 2H and 7.17-6.97 (m) 3H ($C_6H_5$), 5.77 (dd J = 9.5 Hz), 5.63 (d J = 4 Hz) ($H_{1\beta}$), 5.82-3.83 (series of multiplets) 35H (OCH, OCH$_2$) and 2.23-1.93 ppm (series of singlets) 48H (CH$_3$CO).

Pure phenylhexadecaacetylmaltopentaoside was obtained from the above solid product by HPLC using columns packed with >40μ silica gel spheres with a mobile phase of 1% methanol, 49% pentane, and 50% dichloromethane. Integration of the 220 MHz $^1$H nmr spectrum showed that this material consisted of ca. 75% α-phenylhexadecaacetylmaltopentaoside and 25% β-phenylhexadecaacetylmaltopentaoside.

(C) Preparation of α- and β-Phenylhexadecaacetylmaltopentaoside (Alternate Method)

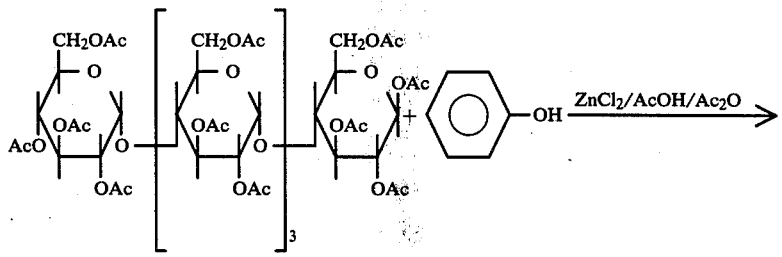

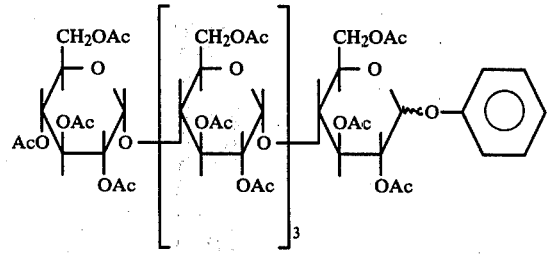

A mixture of maltopentaose β-heptadecaacetate from part (A) (3.00 g, 1.95 mmole) and phenol (1.95 g, 20.8 mmmole) in a 3-neck flask under nitrogen was treated with a solution of zinc chloride (0.49 g) in 2.0 ml of a mixture of 95:5 acetic acid:acetic anhydride, and the reaction mixture was slowly warmed. When the reaction mixture became homogeneous, the internal pressure was gradually reduced to 23 mm and the mixture was stirred at 100° for 2.5 hr. The residue was treated with benzene (200 ml) and 18% aqueous sodium chloride solution. The organic phase was washed twice with 2.5% sodium hydroxide (50 ml) and twice with saturated sodium chloride (50 ml). The organic layer was dried over sodium sulfate, evaporated, and the residue treated with anhydrous sodium acetate (3.0 g) and acetic anhydride (15 ml). The mixture was heated at 120° for 1.0 hr, cooled, and treated with ice water (200 ml). The solid product which formed upon standing at 0° was pulverized, filtered, and air dried to give 2.97 g of an off-white powder. This material was chromatographed on a silica gel column eluting with a mixture of 97:3 benzene:methanol. There was obtained a total of 2.00 g (65%) of pure α- and β-phenylhexadecaacetylmaltopentaoside, mp 119°–125°; $[\alpha]_D^{25°} + 137°$ (c 1.0, chloroform);

Anal. Calcd for $C_{68}H_{88}O_{42}$: C, 51.77; H, 5.62. Found: C, 51.62, 51.13; H, 5.70, 5.47.

(D) Preparation of (4-Nitrophenyl)hexadecaacetylmaltopentaoside

A slurry of nitronium tetrafluoroborate (0.85 g, 6.4 mmole) in dry dichloromethane (10 ml) under an argon atmosphere was treated with a solution of phenylhexadecaacetylmaltopentaoside from part (C) (1.00 g, 0.64 mmole) in dichloromethane (12 ml). The resulting mixture was stirred for 20 min at room temperature, poured into stirred, cold, saturated sodium chloride solution (70 ml), and the separated organic layer dried over magnesium sulfate. Evaporation of solvent under reduced pressure gave a yellow solid (1.05 g) which was recrystallized from ethanol (30 ml) to provide 0.87 g of an off-white powder. The product structure was confirmed by $\lambda_{max}^{CH3OH}$ 290 nm (ε 5550), 210 nm (ε 7750); $^1H$ nmr spectrum (220 MHz) δ 7.75 (AA'BB', $J_{AB}$ = 9.5 Hz) 4H ($C_6H_4$), 5.75 (d J = 4 Hz) ($H_{1\beta}$), 5.78-3.85 (series of multiplets) (OCH, $OCH_2$), and 2.22-1.93 ppm (series of singlets) 48H ($CH_3CO$).

Two recrystallizations of the crude (4-nitrophenyl)-hexadecaacetylmaltopentaoside from ethanol gave a sample with $\lambda_{max}^{CH3OH}$ 290 nm (ε 6650) and 212 (7700).

(E) Preparation of (4-Nitrophenyl)maltopentaoside

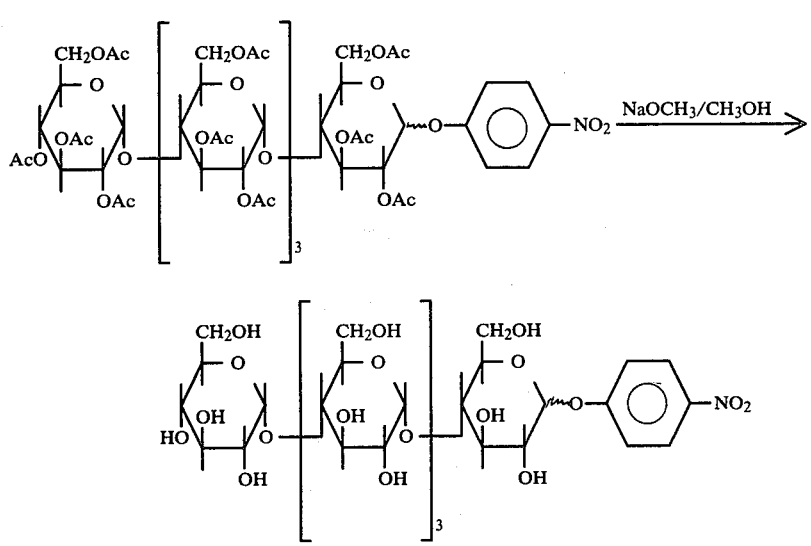

A solution of (4-nitrophenyl)hexadecaacetylmaltopentaoside from part (D) (430 mg, 0.27 mmole) in methanol (5 ml) was treated with a solution of sodium methoxide in methanol (4.7 ml of $7.8 \times 10^{-4}$ M), and then stirred for 17.5 hr at room temperature. The solution was concentrated under a stream of dry nitrogen,

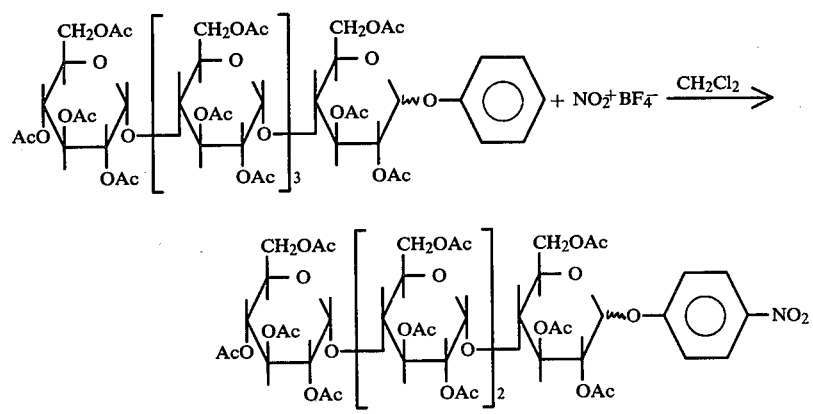

and the stirred residue was treated with ether (40 ml) to precipitate a solid which was filtered and air-dried to provide a slightly yellow powder (247 mg, 98%), $\lambda_{max}$ ($H_2O$) 303 nm (ε 5980), 215 (5530). HPLC (Waters Associates μ Bondapak/Carbohydrate, 80% acetonitrile/water, 254 nm UV detector) of the product showed two equally intense peaks with retention times 10.9 and 12.3 min corresponding to 4-(nitrophenyl)maltopentaoside and an unidentified material.

(F) Preparation of α-and
β-(4-Nitrophenyl)maltopentaoside

EXAMPLES 3-32

In Table II, when the phenol of Examples 1 and 2 is replaced as the reactant by the substituted phenols listed in Column A, the mixed α- and β- (substituted aryl)-polyacetyl glycosides listed in Column B are obtained by the procedures of Examples 1(B) or (C) or 2(B) or (C). Nitration of the products of Column B by the pro-

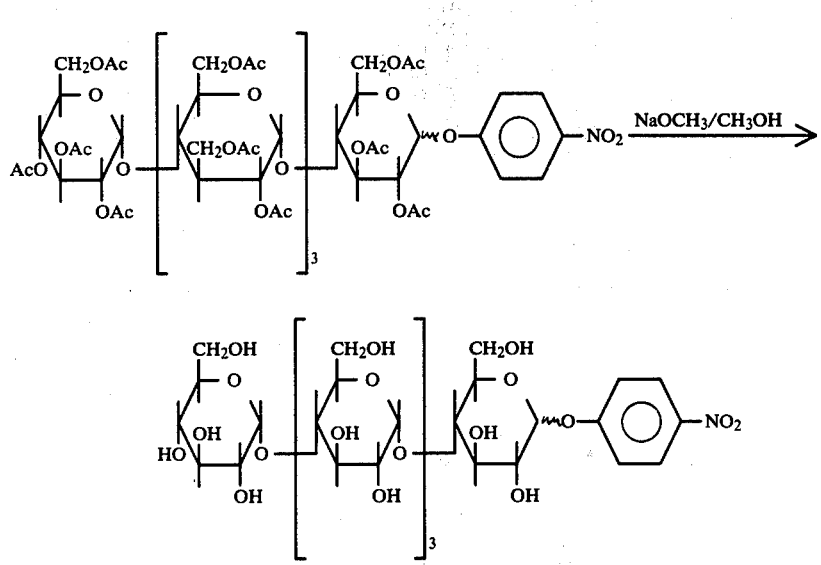

(4-Nitrophenyl)hexadecaacetylmaltopentaoside (6.1 g, 3.8 mmol, prepared as described in part D, was mixed with methanol (150 ml) and treated with 4.1 ml of 0.15 M sodium methoxide in methanol (0.62 mmol). The resulting yellow solution was stirred for 22 hr at room temperature. The solution was neutralized with 1% hydrogen chloride in methanol and the solvent was partially removed under reduced pressure to initiate precipitation. The remaining solution was added slowly to 370 ml diethyl ether with vigorous magnetic stirring. The mixture was stirred for an additional hour to allow for complete precipitation. Filtration and suction drying under an atmosphere of nitrogen provided 3.24 g (90%) of cream-colored solid. $\lambda_{H_2O}^{max}$ 303 ($\epsilon$ = 7310), 217 ($\epsilon$ 5385). HPLC (propylethylenediamine modified silica (8μ particles), 4.1 mm i.d. × 25 cm, 25/75 H$_2$O/CH$_3$CN, 254 nm detector) showed two major components, 56% and 30%, identified as α and β isomers of (4-nitrophenyl)maltopentaoside in a 65/35 ratio.

A portion of this material was chromatographed on Sephadex ® G-15 and eluted with water to provide a center cut which was lyophilized to give a cream-colored solid. This sample exhibited $\lambda_{max}^{H_2O}$ 303 ($\epsilon$ = 9160), 219 ($\epsilon$ = 6590). HPLC showed two major components, 66% and 30%. $^1$H nmr (220 mHz) recorded in D$_2$O: 7.72 (center of aryl AA'BB' pattern, J$_{AB}$ = 9.5 Hz), 5.76 (d, J = 4 Hz, H$_1$, of α isomer), 5.45-5.27 (m, HC(OR) (OR')), 4.23-3.32 (m, CH and CH$_2$). The α/β ratio was ca. 62/38.

cedures of Examples 1(D) or (E) or 2(D) gives the mixed α- and β- (substituted nitroaryl)-polyacetyl glycosides listed in Column C. Deacetylation of the products of Column C by the procedures of Examples 1(F), (G) or (H), or 2(E) gives the mixed α- and β- (substituted nitroaryl)glycosides listed in Column D.

Maltohexaose β-eicosaacetate (G$_6$Ac$_{20}$) can be prepared by acetylation of maltohexaose according to the procedures of Examples 1(A) and 2(A). Maltotetraose, maltopentaose and maltohexaose are prepared as described earlier.

In Column A of Table II, the following starting materials are available commercially: 2-, 3-, or 4-methylphenol (o-, m-, and p-cresol), 2-, 3- and 4-chlorophenol, 2-fluorophenol, 3-bromophenol, 4-iodophenol, 2-, 3- and 4-nitrophenol, 4-methoxyphenol, 2-isopropyl-5-methylphenol (thymol), methyl salicylate, 3-ethylphenol, 4-t-butylphenol, 1- and 2-naphthol, 4-chloro-1-naphthol, and 4-hydroxybenzoic acid (for the preparation of hexyl 4-hydroxybenzoate). The following starting materials are all described in "Dictionary of Organic Compounds", 4th Ed., edited by I. Heilborn, Oxford University Press (1965) on the pages indicated: 2-methyl-5-isopropylphenol (carvacrol, p. 568), 2-methoxyphenol (guaiacol, p. 1549), and 3-methoxyphenol (p. 2857). Hexyl 4-hydroxybenzoate can be made by the acid-catalyzed esterification of 4-hydroxybenzoic acid with 1-hexanol using the procedure given for methyl salicylate by A. I. Vogel "Practical Organic Chemistry", 3rd Edition, Longmans Green, London, 1959, p. 782.

TABLE II

| | α- and β-(Substituted Nitroaryl) Glycosides | |
|---|---|---|
| Example | Column A | Column B |
| 3 | 2-CH$_3$C$_6$H$_4$OH | G$_4$(Ac)$_{13}$(2-CH$_3$C$_6$H$_4$) |
| 4 | 3-CH$_3$C$_6$H$_4$OH | G$_4$(Ac)$_{13}$(3-CH$_3$C$_6$H$_4$) |
| 5 | 4-CH$_3$C$_6$H$_4$OH | G$_5$(Ac)$_{16}$(4-CH$_3$C$_6$H$_4$) |
| 6 | 2-ClC$_6$H$_4$OH | G$_5$(Ac)$_{16}$(2-ClC$_6$H$_4$) |

TABLE II-continued

| | | |
|---|---|---|
| 7 | 3-ClC$_6$H$_4$OH | G$_5$(Ac)$_{16}$(3-ClC$_6$H$_4$) |
| 8 | 4-ClC$_6$H$_4$OH | G$_4$(Ac)$_{13}$(4-ClC$_6$H$_4$) |
| 9 | 2-FC$_6$H$_4$OH | G$_4$(Ac)$_{13}$(2-FC$_6$H$_4$) |
| 10 | 3-BrC$_6$H$_4$OH | G$_5$(Ac)$_{16}$(3-BrC$_6$H$_4$) |
| 11 | 4-IC$_6$H$_4$OH | G$_4$(Ac)$_{13}$(4-IC$_6$H$_4$) |
| 12 | 2-O$_2$NC$_6$H$_4$OH | G$_4$(Ac)$_{13}$(2-O$_2$NC$_6$H$_4$) |
| 13 | 3-O$_2$NC$_6$H$_4$OH | G$_5$(Ac)$_{16}$(3-O$_2$NC$_6$H$_4$) |
| 14 | 4-O$_2$NC$_6$H$_4$OH | G$_5$(Ac)$_{16}$(4-O$_2$NC$_6$H$_4$) |
| 15 | 2-CH$_3$OC$_6$H$_4$OH | G$_4$(Ac)$_{13}$(2-CH$_3$OC$_6$H$_4$) |
| 16 | 3-CH$_3$OC$_6$H$_4$OH | G$_5$(Ac)$_{16}$(3-CH$_3$OC$_6$H$_4$) |
| 17 | 4-CH$_3$OC$_6$H$_4$OH | G$_4$(Ac)$_{13}$(4-CH$_3$OC$_6$H$_4$) |
| 18 | 2-CH$_3$-5-(CH$_3$)$_2$CHC$_6$H$_3$OH | G$_4$(Ac)$_{13}$(2-CH$_3$-5-(CH$_3$)$_2$CHC$_6$H$_3$) |
| 19 | 2-(CH$_3$)$_2$CH-5-CH$_3$C$_6$H$_3$OH | G$_5$(Ac)$_{16}$(2-(CH$_3$)$_2$CH-5CH$_3$C$_6$H$_3$) |
| 20 | 2-CH$_3$O$_2$CC$_6$H$_4$OH | G$_4$(Ac)$_{13}$(2-CH$_3$O$_2$CC$_6$H$_4$) |
| 21 | 3-C$_2$H$_5$C$_6$H$_4$OH | G$_5$(Ac)$_{16}$(3-C$_2$H$_5$C$_6$H$_4$) |
| 22 | 4-t-C$_4$H$_9$C$_6$H$_4$OH | G$_4$(Ac)$_{13}$(4-t-C$_4$H$_9$C$_6$H$_4$) |
| 23 | 1-naphthol | G$_4$(Ac)$_{13}$(1-C$_{10}$H$_7$) |
| 24 | 2-naphthol | G$_4$(Ac)$_{13}$(2-C$_{10}$H$_7$) |
| 25 | 4-chloro-1-naphthol | G$_4$(Ac)$_{13}$(4-Cl-1-C$_{10}$H$_7$) |
| 26 | 4-C$_6$H$_{13}$CO$_2$C$_6$H$_4$OH | G$_4$(Ac)$_{13}$(4-C$_6$H$_{13}$CO$_2$C$_6$H$_4$) |
| 27 | 3-CH$_3$C$_6$H$_4$OH | G$_6$(Ac)$_{19}$(3-CH$_3$C$_6$H$_4$) |
| 28 | 2-ClC$_6$H$_4$OH | G$_6$(Ac)$_{19}$(2-ClC$_6$H$_4$) |
| 29 | 3-O$_2$NC$_6$H$_4$OH | G$_6$(Ac)$_{19}$(3-O$_2$NC$_6$H$_4$) |
| 30 | 2-CH$_3$OC$_6$H$_4$OH | G$_6$(Ac)$_{19}$(2-CH$_3$OC$_6$H$_4$) |
| 31 | 1-naphthol | G$_6$(Ac)$_{19}$(1-C$_{10}$H$_7$) |
| 32 | C$_6$H$_5$OH | G$_6$(Ac)$_{19}$(C$_6$H$_5$) |

| Example | Column C | Column D |
|---|---|---|
| 3 | G$_4$(Ac)$_{13}$(2-CH$_3$-4-O$_2$NC$_6$H$_3$) | G$_4$(2-CH$_3$-4-O$_2$NC$_6$H$_3$) |
| 4 | G$_4$(Ac)$_{13}$(3-CH$_3$-4-O$_2$NC$_6$H$_3$) | G$_4$(3-CH$_3$-4-O$_2$NC$_6$H$_3$) |
| 5 | G$_5$(Ac)$_{16}$(4-CH$_3$-2-O$_2$NC$_6$H$_3$) | G$_5$(4-CH$_3$-2-O$_2$NC$_6$H$_3$) |
| 6 | G$_5$(Ac)$_{16}$(2-Cl-4-O$_2$NC$_6$H$_3$) | G$_5$(2-Cl-4-O$_2$NC$_6$H$_3$) |
| 7 | G$_5$(Ac)$_{16}$(3-Cl-4-O$_2$NC$_6$H$_3$) | G$_5$(3-Cl-4-O$_2$NC$_6$H$_3$) |
| 8 | G$_4$(Ac)$_{13}$(4-Cl-2-O$_2$NC$_6$H$_3$) | G$_4$(4-Cl-2-O$_2$NC$_6$H$_3$) |
| 9 | G$_4$(Ac)$_{13}$(2-F-4-O$_2$NC$_6$H$_3$) | G$_4$(2-F-4-O$_2$NC$_6$H$_3$) |
| 10 | G$_5$(Ac)$_{16}$(3-Br-4-O$_2$NC$_6$H$_3$) | G$_5$(3-Br-4-O$_2$NC$_6$H$_3$) |
| 11 | G$_4$(Ac)$_{13}$(4-I-2-O$_2$NC$_6$H$_3$) | G$_4$(4-I-2-O$_2$NC$_6$H$_3$) |
| 12 | G$_4$(Ac)$_{13}$[2,4-(O$_2$N)$_2$C$_6$H$_3$] | G$_4$[2,4-(O$_2$N)$_2$C$_6$H$_3$] |
| 13 | G$_5$(Ac)$_{16}$[3,5-(O$_2$N)$_2$C$_6$H$_3$] | G$_5$[3,5-(O$_2$N)$_2$C$_6$H$_3$] |
| 14 | G$_5$(Ac)$_{16}$[2,4-(O$_2$N)$_2$C$_6$H$_3$] | G$_5$[2,4-(O$_2$N)$_2$C$_6$H$_3$] |
| 15 | G$_4$(Ac)$_{13}$(2-CH$_3$O-4-O$_2$NC$_6$H$_3$) | G$_4$(2-CH$_3$O-4-O$_2$NC$_6$H$_3$) |
| 16 | G$_5$(Ac)$_{16}$(3-CH$_3$O-4-O$_2$NC$_6$H$_3$) | G$_5$(3-CH$_3$O-4-O$_2$NC$_6$H$_3$) |
| 17 | G$_4$(AC)$_{13}$(4-CH$_3$O-2-O$_2$NC$_6$H$_3$) | G$_4$(4-CH$_3$O-2-O$_2$NC$_6$H$_3$) |
| 18 | G$_4$(Ac)$_{13}$(2-CH$_3$-5-(CH$_3$)$_2$CH-4-O$_2$NC$_6$H$_2$) | G$_4$(2-CH$_3$-5-(CH$_3$)$_2$CH-4-O$_2$NCH$_2$) |
| 19 | G$_5$(Ac)$_{16}$(2-(CH$_3$)$_2$CH-5-CH$_3$-4-O$_2$NC$_6$H$_2$) | G$_5$(2-(CH$_3$)$_2$CH-5-CH$_3$-4-O$_2$NC$_6$H$_2$) |
| 20 | G$_4$(Ac)$_{13}$(2-CH$_3$O$_2$C-4-O$_2$NC$_6$H$_3$) | G$_4$(2-CH$_3$O$_2$C-4-O$_2$NC$_6$H$_3$) |
| 21 | G$_5$(Ac)$_{16}$(3-C$_2$H$_5$-4-O$_2$NC$_6$H$_3$) | G$_5$(3-C$_2$H$_5$-4-O$_2$N$_6$H$_3$) |
| 22 | G$_4$(Ac)$_{13}$(4-t-C$_4$H$_9$-2-O$_2$NC$_6$H$_3$) | G$_4$(4-t-C$_4$H$_9$-2-O$_2$NC$_6$H$_3$) |
| 23 | G$_4$(Ac)$_{13}$(4-O$_2$N-1-C$_{10}$H$_7$) | G$_4$(4-O$_2$N-1-C$_{10}$H$_7$) |
| 24 | G$_4$(Ac)$_{13}$(1-O$_2$N-2-C$_{10}$H$_7$) | G$_4$(1-O$_2$N-2-C$_{10}$H$_7$) |
| 25 | G$_4$(Ac)$_{13}$(4-Cl-2-O$_2$N-1-C$_{10}$H$_7$) | G$_4$(2-NO$_2$-4-Cl-1-C$_{10}$H$_7$) |
| 26 | G$_4$(Ac)$_{13}$(2-O$_2$N-4-C$_6$H$_{13}$CO$_2$C$_6$H$_3$) | G$_4$(2-O$_2$N-4-C$_6$H$_{13}$CO$_2$C$_6$H$_3$) |
| 27 | G$_6$(Ac)$_{19}$(3-CH$_3$-4-O$_2$NC$_6$H$_3$) | G$_6$(3-CH$_3$-4-O$_2$NC$_6$H$_3$) |
| 28 | G$_6$(Ac)$_{19}$(2-Cl-4-O$_2$NC$_6$H$_3$) | G$_6$(2-Cl-4-O$_2$NC$_6$H$_3$) |
| 29 | G$_6$(Ac)$_{19}$(3,5-(O$_2$N)$_2$C$_6$H$_3$) | G$_6$(3,5-(O$_2$N)$_2$C$_6$H$_3$) |
| 30 | G$_6$(Ac)$_{19}$(2-CH$_3$O-4-O$_2$NC$_6$H$_3$) | G$_6$(2-CH$_3$O-4-O$_2$NC$_6$H$_3$) |
| 31 | G$_6$(Ac)$_{19}$(4-O$_2$N-1-C$_{10}$H$_7$) | G$_6$(4-O$_2$N-1-C$_{10}$H$_7$) |
| 32 | G$_6$(Ac)$_{19}$(4-O$_2$NC$_6$H$_4$) | G$_6$(4-O$_2$NC$_6$H$_4$) |

What is claimed is:

1. A process for preparing α and β nitroaromatic glycosides comprising:

(a) contacting an acetylated glycoside of the formula:

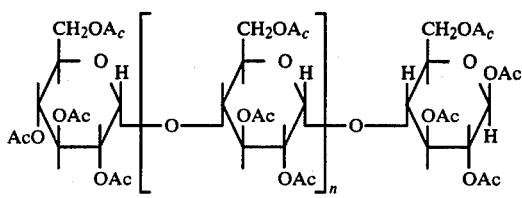

wherein Ac is an acetyl group, and n is an integer of 2, 3 or 4, with a phenol selected from the group consisting of

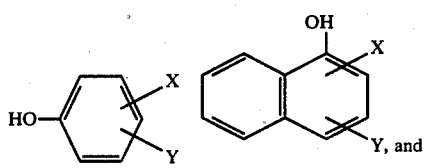

wherein X and Y are individually H, $NO_2$, halogen, alkyl of 1 to 4 carbon atoms, OR' or $CO_2R'$ where R' is an alkyl group of 1 to 6 carbon atoms, with the proviso that only one of X and Y is $NO_2$, in the presence of a catalyst at a temperature in the range of about 80°–120° C;

(b) nitrating the product of (a) by contacting said product with:
  (i) nitric acid contained in a mixture of acetic acid and sulfuric acid, or
  (ii) a nitronium compound selected from nitronium tetrafluoroborate, nitronium hexafluorophosphate and nitronium trifluoromethanesulfonat contained in dichloromethane, chloroform or 1,2-dichloroethane; and (c) deacetylating the product of (b) by contacting said product with:
  (i) a catalytic amount of an alkali metal lower alkoxide contained in the corresponding alcohol, or
  (ii) a solution of anhydrous ammonia or HCl in methanol.

2. The process of claim 1 wherein the phenol is

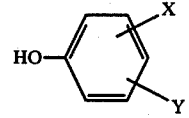

3. The process of claim 2 wherein n is 2 or 3.

4. The process of claim 3 wherein the catalyst in step (a) is p-toluenesulfonic acid, or an anhydrous covalent metal chloride.

5. The process of claim 4 wherein the anhydrous covalent metal chloride is zinc chloride.

6. The process of claim 4 wherein the temperature in step (a) is in the range of about 100°–110° C.

7. The process of claim 4 wherein the nitration reaction of step (b) comprises contacting the product of step (a) with nitronium tetrafluoroborate contained in dichloromethane, chloroform or 1,2-dichloroethane at a temperature of about 25° C., the molar ratio of nitronium tetrafluoroborate to step (a) product being in the range of 1–20:1.

8. The process of claim 7 wherein the nitronium tetrafluoroborate is contained in dichloromethane and the molar ratio is about 10:1.

9. The process of claim 4 wherein the deacetylation reaction of step (c) comprises contacting the product of step (b) with about 0.01–0.1 molar equivalent of sodium methoxide contained in methanol at a temperature in the range of about 0°–25° C.

10. The process of claim 7 wherein the deacetylation reaction of step (c) comprises contacting the product of step (b) with about 0.01–0.1 molar equivalent of sodium methoxide contained in methanol at a temperature in the range of about 0°–25° C.

* * * * *